United States Patent [19]

Kienecker et al.

[11] Patent Number: 4,784,873

[45] Date of Patent: Nov. 15, 1988

[54] METHOD OF PRODUCING BIOLOGICAL SPECIMENS

[75] Inventors: Wilhelm Kienecker; Klaus Uhlmann, both of, Bad Homburg, Fed. Rep. of Germany

[73] Assignee: Arthur Pfeiffer Vakuumtechnik Wetzlar GmbH, Asslar, Fed. Rep. of Germany

[21] Appl. No.: 605,614

[22] Filed: Apr. 30, 1984

[30] Foreign Application Priority Data

May 30, 1983 [DE] Fed. Rep. of Germany ....... 3319564

[51] Int. Cl.$^4$ .......................... A01N 1/02; A01G 5/06
[52] U.S. Cl. ............................................. 427/2; 427/4
[58] Field of Search ............................ 427/4, 2; 424/3

[56] References Cited

U.S. PATENT DOCUMENTS

| | | | |
|---|---|---|---|
| 3,961,097 | 6/1976 | Gravlee | 424/3 X |
| 4,205,059 | 5/1980 | Hagens | 427/4 |
| 4,353,856 | 10/1982 | Mack et al. | 424/3 X |
| 4,497,792 | 2/1985 | Gindler | 427/4 X |
| 4,510,169 | 4/1985 | Linner | 427/4 |

Primary Examiner—Michael R. Lusignan
Attorney, Agent, or Firm—Toren, McGeady & Associates

[57] ABSTRACT

In a method of producing flexible and durable biological specimens, tissue water and any preservative which may be present is replaced by one or more water-soluble impregnating agents by direct molecular substitution without any intermedium or solvent and without removing the tissue lipides. Polyethylene glycol may be used as the impregnating agent. The replacement preferably occurs under vacuum and the specimen may be subsequently sealed.

1 Claim, No Drawings

METHOD OF PRODUCING BIOLOGICAL SPECIMENS

BACKGROUND OF THE INVENTION

The invention relates to a method of giving preserved and non-preserved biological material endurance strength while retaining its natural size, consistency, dissecting capacity, plasticity, flexibility as well as internal and external structure.

For teaching and demonstration purposes as well as for museum archiving, particularly in anatomy, pathology and biology and their fringe areas, either so-called moist specimens or artificial models are used. Moist specimens have the disadvantage that they always have to be kept in preserving liquid and can only be removed briefly from this liquid for demonstration purposes. Artificial models are imitations of natural specimens and have the defects of inadequate fidelity of imitation, unnatural consistency, lack of flexibility and absence of dissecting capacity. For the production of natural demonstrated, there have hitherto also been the following possibilities:

1. The storage of the materials in preserving liquids in glass vessels, so-called wet specimens,
2. the drying of the specimens,
3. the freeze-drying of the specimens,
4. the paraffining of dried or freeze-dried specimens,
5. the embedding of plastics-impregnated objects in transparent blocks of plastics material,
6. preserving sections of biological objects by means of a mounting medium between 2 glass supports or between foils,
7. encasing specimens in plastics materials,
8. the methods of giving specimens endurance strength by impregnation of the objects either directly or indirectly via intermedia by means of synthetic resins.

The methods given above are as follows:

Method 1

Wet specimens are stored in a preserving liquid in glass containers. The preserving liquid must be renewed at regular intervals and the specimen is mechanically secured inside the glass vessel for demonstration purposes. With this kind of storage of demonstration material there is the disadvantage that the specimens can only be observed from outside and cannot be handled and manipulated. Superficial structures and structures in depth appear distorted as a result of the media diffracting differently. In addition, the specimens lose their natural colouring.

Method 2

The drying of biological specimens can only be carried out with small objects because a shrinkage of the material occurs as a result of the drying. The specimens thus produced also have the disadvantage that they can very easily be damaged by mechanical effects.

Method 3

It is true that freeze-dried biological specimens do not shrink, in contrast to dried specimens, and retain their shape, but they are 1. extremely sensitive to external mechanical effects and
2. the consistency of the tissue is altered considerably by the freeze-drying in the sense of hardening of the tissue.

Method 4

Paraffin-impregnated specimens do not permit a clear detailed representation of the surface because paraffin is not transparent. In addition, such specimens are very liable to break and can only be kept clean with great expense.

Method 5

Specimens embedded in plastics material correspond in form to the wet specimens described under Method 1 but have the advantage in comparison with these that blocks of plastics material are more secure against breakage and the specimen is insensitive to external influences and a result of the embedding in the plastics material.

Method 6

Sections of specimens which are introduced between glass plates or foils have the disadvantage of a great risk of breakage and little flexibility.

Method 7

According to U.S. Pat. No. 2,698,809 there is disclosed a method for the external embedding of biological materials wherein the specimens are encased in plastics material while retaining satisfactory colour. With this method of treatment, the embedding agent does not penetrate into the specimen (Lit. Science Vol. 54,49–50, 1941). As a result of the hardening, objects thus treated are stiffened in their consistency, lose their plasticity and subsequently can no longer be dissected.

Method 8

The methods disclosed in German Patent specification No. 27 10147,9–41 for the permanent preservation of specimens of biological objects liable to decay and methods of producing them are suitable for demonstrating their exposed surfaces. The specimens can be felt and also observed through a magnifying glass. They have the disadvantage, however, that after the production of the specimen, dissecting that is to say a further systematic analysis of the specimen, is not possible, the consistency of the specimen no longer corresponds to its original one, the plasticity and flexibility of the tissue have altered considerably from its original state and the methods of production through intermedia or other solvents and the embedding in plastics materials are very time-consuming, expensive and suffer from a factor of uncertainty in the uniform production of specimens caused by the different hardening of plastics materials as a result of minor alternations in the amounts of synthetic resin components.

All the above methods of giving biological objects endurance strength suffer from drawbacks, because they lead to an alteration in the consistency as a result of homogenization of the tissues through the embedding agent combined with a more or less severe loss of plasticity and flexibility. In addition, a subsequent dissecting of the biological specimens thus treated is no longer possible. Furthermore, the methods of production are technically very extravagant and very expensive through the use of special chemicals for the impregnation and embedding.

SUMMARY OF THE INVENTION

The present invention seeks to produce extremely cheap biological specimens which can be kept indefinitely and which correspond, in their size, consistency, plasticity, dissecting capacity, flexibility and internal and external structure to the natural state. In addition, the size of the objects to be treated should not preset any limiting factor for the method. Biochemical and technical theory forms the principle for the solution of this problem.

The present invention provides a method of producing durable flexible biological specimens from initial specimens which contain tissue water, the method comprising the step of replacing the tissue water in the original specimens by one or more water-soluble impregnating agents by direct molecular substitution.

DESCRIPTION OF THE PREFERRED EMBODIMENTS

Basically the present invention provides a method of producing flexible biological specimens with durability comprising replacing the tissue water and any preservative which may be present by one or more water-soluble impregnating agents by direct molecular substitution.

Thus the decisive point for giving biological materials endurance strength lies in the complete extraction of the tissue water and any preservative so that no further metabolic processes can subsequently alter the tissue. Since the extraction of the tissue water and any preservatives by drying, freezing-drying or by exchange via intermedia with following embedding in plastics materials leads to alterations in consistency, size, plasticity and flexibility, such techniques are not suitable for the solution to the problem. In addition, apart from the requirement of the extraction of the tissue water and any preservatives, there is also the problem of introducing an embedding medium which is neutral with regard to consistency and flexibility into the biological specimen, which must also be able to be removed again at any time if desired. These requirements firstly presuppose that the embedding medium must be miscible with water in any proportion and secondly there must be a direct molecular substitution by the embedding medium for the tissue water and any preservative to be removed. Thus in a method according to the invention, this problem is solved in that the tissue water and any preservative which may be present is replaced, under vacuum, by water-soluble impregnating agent, without any intermedium or solvent and without removing the tissue lipides, by direct molecular substitution.

Polyethylene glycol is particularly suitable as an embedding medium and has the further advantage of being able to be used in various molecular weights and so different consistencies which can be controlled, depending on heat, during the molecular substitution. A further advantage of polyethylene glycol is its cheapness. The problem of the molecular substitution can now be solved by the fact that the tissue water and any preserving liquids have a considerably higher vapour pressure than polyethylene glycol. As a result there is the possibility of direct distillation of the tissue water and any preserving liquids and immediate molecular replacement by polyethylene glycol. This prevents a change in volume and consistency of the biological objects thus treated. Since polyethylene glycol is a chemically inert substance, no secondary chemical changes are caused to the specimens as with the methods hitherto known. The consequence of this is that a complete fidelity of the specimen to the original is achieved by this method.

The molecular substitution presupposes a distillation of the tissue water and any preserving liquid. This is accomplished by a constant negative alteration or adjustment of the partial pressure drop of the tissue water and any preserving agent. This process of the distillation of the tissue water and any preservative and its molecular substitution by polyethylene glycol can be accelerated if it is allowed to take place under vacuum.

The use of a vacuum leads to an exponential increase in the speed of the molecular substitution according to the vapour pressure drop of the tissue water and any preserving liquids depending on the throughput of the vacuum pumps used. The use of this technique further leads to the fact that the tissue water and any preserving liquids are also removed from the excess embedding medium (polyethylene glycol) so that this is retained in pure form and so can be further used without loss. Since, after carrying out the molecular substitution, no further treatment is necessary (such as polymerisation which is used in other known methods), no further shrinkage or change in consistency occurs either. Thus the method described above for giving preserved and non-preserved biological materials endurance strength represents an optimum not hitherto known for retaining the natural size, consistency, dissecting capacity, plasticity, flexibility, internal and external structure. It must be emphasized in particular that the mobility of articulate connections in particular is fully retained, which was hitherto quite impossible with permanent specimens because all previously known methods led to a shrinkage and hardening of the articulate soft parts.

Furthermore the characteristic of polyethylene glycol in contrast to preservatives and synthetic resin embedding agents, of not being harmful to health is not insignificant. This means a simple method of handling such material for the user.

The practical application of the invention is described below with reference to examples:

1. Product of a fully movable operational specimen of a human knee joint

The knee joint of a formalin-fixed dissecting-room body is processed to form a ligament specimen. Without further prior treatment, this is introduced into a pressure-resistant container, which is partially filled with liquid polyethylene glycol 400, and is submerged therein. The container, which is closed in an airtight manner, is evacuated with a vacuum pump for several hours until the water has been completely substituted by polyethylene glycol. The specimen, which is now impregnated with polyethylene glycol, is taken out of the container and stored on an absorbent support until the excess polyethylene glycol adhering externally has completely run off. The specimen can be sprayed with PVC spray to protect and seal the surface.

2. Production of a flexible organ specimen of the heart

For the dissection of a formalin-fixed heart with exhibition of the superficial musculature and the coronary vessels, walls of the atria are cut into and folded out. Without further preliminary treatment, this moist specimen is treated as described under Example 1.

3. Production of a foot specimen given endurance strength and able to be dissected.

An amputated foot preserved in formalin is treated as described under Example 1 and then dissected anatomically in the usual manner. The dissection characteristics of the tissue are considerably improved in comparison with a moist specimen which is only formalin-fixed, in the following points:

(a) The adipose tissue is stabilized so that there is scarcely any outflow of fat, as otherwise usual.
(b) The nerve tissue is resistant to tearing and can be dissected as far as the individual nerve fibres so that even the finest branches of nerves can be exhibited far into the periphery. This is not possible with conventional specimens.

(c) The softer connective tissue appears fine-fibred in accordance with its natural construction and is not homogeneously jelly-like as in the usual specimens.

(d) As a result of the stabilization of their wall structures, the blood vessels again appear in their natural round shape, that is to say they are not collapsed as in the usual moist specimens.

(e) The musculature almost recovers the brownish-red colour of the living tissue whereas the normally preserved specimens are greatly faded.

(f) All the other tissue structures can likewise be better dissected and exhibited.

It will be understood that the above description of the present invention is susceptible to various modifications, changes and adaptations.

What is claimed is:

1. A method for producing durable, flexible biological specimens from initial specimens containing tissue water comprising, removing the tissue water from the specimen in a vacuum and simultaneously treating the specimen with a water-soluble impregnating agent being polyethylene glycol having a vapor pressure lower than tissue water, regulating the vacuum pressure by continuous negative adjustment of the partial pressure gradient of the tissue water so that the tissue water is evaporated at a rate which allows direct and continuous substitution of the tissue water by the impregnating agent.

* * * * *